United States Patent [19]

Williams et al.

[11] Plant 4,320

[45] Oct. 24, 1978

[54] APPLE TREE (COOP 14)

[75] Inventors: Edwin B. Williams, Lafayette; Jules Janick; Frank H. Emerson, both of West Lafayette, all of Ind.; Daniel F. Dayton, Urbana, Ill.; L. Fredric Hough, Bloomsbury; Catherine H. Bailey, Englishtown, both of N.J.

[73] Assignee: Purdue Research Foundation, West Lafayette, Ind.

[21] Appl. No.: 821,641

[22] Filed: Aug. 4, 1977

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

This invention relates to a new cultivar of apple tree which is scab resistant, and characterized by a maturity about 6 weeks before Delicious and about 2½ weeks before Prima.

5 Drawing Figures

1

This invention is a new and distinct cultivar of apple trees. It was discovered by applicants in August, 1964, at Urbana, Ill., in the course of an attempt to develop improved apple trees with high fruit quality and resistance to *Venturia inaequalis* (Cke.) Wint., the causal agent for the apple scab disease. The tree is a seedling of known parentage planted in 1959 in the S80E Breeding Orchard of the Department of Horticulture at the Illinois Agricultural Experiment Station, Urbana, Ill. In the above orchard, its position was Row 29, Tree 157, having the description PRI 1325-101 in our breeding records.

The present new cultivar, which is designated as Coop 14, is a seedling produced from crossing the seedling PRI 10-147 as the seed parent and 'Mollie's Delicious' as the pollen parent in 1958 at Urbana, Illinois. This new cultivar carries a genetic factor, $V_f$, inherited from *Malus floribunda* 821, which causes it to be resistant to infection caused by *Venturia inaequalis.* The presence of this factor has been repeatedly proven by controlled inoculation tests in the Purdue greenhouse of the seedling and off its offspring produced from controlled crosses. The complete pedigree is shown below:

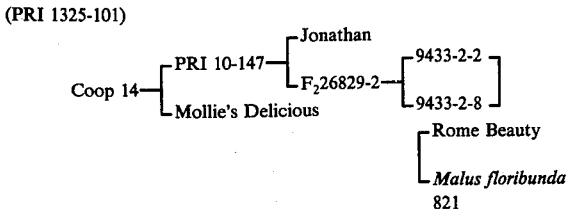

This new cultivar produces a spreading and somewhat dwarfish tree with good annual crops. It is resistant to scab and moderately resistant to fireblight and powdery mildew.

The tree flowers with 'McIntosh' and 'Priscilla' which is described in U.S. Plant Pat. No. 3,488. The apple fruit has very good dessert quality, fruit hold texture and quality 6 weeks or more at 34° F.

After observation, the selection was asexually propagated by grafting on seedling apple roots. The grafted material has maintained the desired characteristics after propagation.

2

The accompanying drawing (color photograph) shows a typical example of fruit and foliage of Coop 14. The following is a detailed description of the new cultivar with the color description according to the Horticultural Colour Chart issued by the British Colour Council in collaboration with the Royal Horticultural Society.

FLOWER

Pedicel: 3 cm (1¼ inches) in length.

Coralla: 5 cm (2 inches) in diameter at enthesis.

Color: Fuchsia purple plate 28/3 (bud) to white (open flowers).

FRUIT

Shape: Ovate, regular.

Size: Axial diameter 7 cm (2¾ inches), transverse diameter 6.5 cm (2⅝ inches).

Color: Undercolor primrose yellow (Plate 601/2), overcolor 75% cardinal red (Plate 622/1).

Skin: Smooth, conspicuous white dots, medium thick, tough, no russeting.

Stem: 2 cm (¾ inch), medium thickness.

Cavity: Acute, shallow, medium width, smooth.

Basin: Medium depth, breadth medium, sides sloping.

Calyx: Persistent, recurved, partly open.

Calyx tube: Urn-shaped.

Stamens: Marginal.

Core line: Meeting.

Core: Medium, open, small.

Carpels: roundish, truncate.

Seed: Acute, not tufted.

Flesh:

*Texture.*—Fine, firm, breaking.

*Quality.*—Very good, mild subacid.

*Color.*—Indian yellow (Plate 6/3).

*Maturity season.*—6 weeks before 'Delicious'.

*Keeping quality.*—Retains quality and texture 6 weeks at 34° F.

*Use.*—Very good dessert apple.

TREE

Tree: Spreading, slightly dwarfish.

Leaves: Oval, double serrate, apex mucronate, base oblique, length to width ratio = 1.9.

In particular our new cultivar apple is distinguished by its resistance to scab and by its very good dessert quality.

We claim:

1. A new and distinct apple tree substantially as shown and described particularly characterized by resistance to apple scab, very good fresh fruit quality, fine flesh texture, and maturity approximately 6 weeks before 'Delicious' and 2½ weeks before 'Prima'.

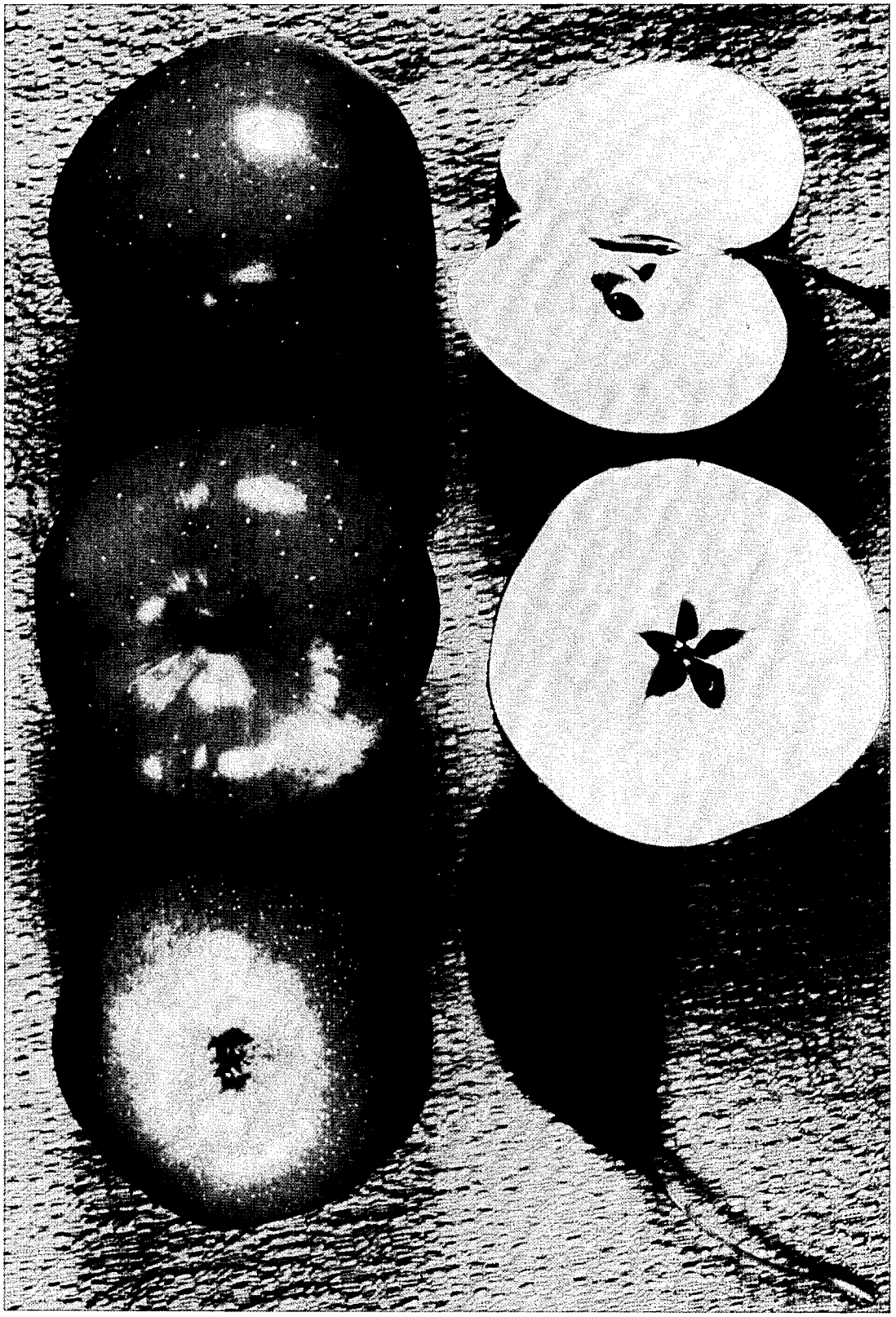

* * * * *